United States Patent [19]
Loeb

[11] Patent Number: 6,112,124
[45] Date of Patent: Aug. 29, 2000

[54] COCHLEAR ELECTRODE ARRAY EMPLOYING DIELECTRIC MEMBERS

[75] Inventor: Gerald E. Loeb, Kingston, Canada

[73] Assignee: Advanced Bionics Corporation, Sylmar, Calif.

[21] Appl. No.: 09/137,033

[22] Filed: Aug. 20, 1998

Related U.S. Application Data

[63] Continuation-in-part of application No. 08/911,804, Aug. 15, 1997, abandoned, which is a continuation-in-part of application No. PCT/US97/00936, Jan. 22, 1997.
[60] Provisional application No. 60/010,494, Jan. 24, 1996.

[51] Int. Cl.[7] .................................................. A61N 1/05
[52] U.S. Cl. ........................................ 607/137; 607/116
[58] Field of Search .................................. 607/116, 137, 607/119, 122, 57; 600/379, 372–374, 377

[56] References Cited

U.S. PATENT DOCUMENTS

| | | |
|---|---|---|
| 4,284,085 | 8/1981 | Hansen et al. . |
| 4,686,765 | 8/1987 | Byers et al. . |
| 4,819,647 | 4/1989 | Byers et al. . |
| 4,832,051 | 5/1989 | Jarvik et al. .................... 607/137 |
| 4,898,183 | 2/1990 | Kuzma . |
| 5,000,194 | 3/1991 | van den Honert et al. . |
| 5,037,497 | 8/1991 | Stypulkowski . |
| 5,443,493 | 8/1995 | Byers et al. . |
| 5,545,219 | 8/1996 | Kuzma . |
| 5,645,585 | 7/1997 | Kuzma . |
| 5,649,970 | 7/1997 | Loeb et al. . |
| 5,653,742 | 8/1997 | Parker et al. .................... 607/137 |

FOREIGN PATENT DOCUMENTS

| | | |
|---|---|---|
| 0002068 | 11/1978 | European Pat. Off. . |
| 0007157 | 5/1979 | European Pat. Off. . |
| 9306698 | 4/1993 | WIPO . |

*Primary Examiner*—George R. Evanisko
*Attorney, Agent, or Firm*—Bryant R. Gold

[57] ABSTRACT

An electrode array (10, 10') for stimulation of the cochlea includes an elongated tapered carrier (15) on which a multiplicity of separately controlled electrode contacts (20) are carried. A set of flexible fins (100, 110, 120) or bumps (120') or other dielectric members extend from the carrier in particular axes so as to cause the outside dimension of the array plus the dielectric members to readily fit within the cavity wherein the array is to be inserted. The dielectric members are made from compliant, dielectric material. When formed as fins, the dielectric members can be folded against the body of the carrier as it is inserted into the cochlea so that they readily slide past obstructions and accommodate variations in the cross-sectional dimensions of the cavity, e.g., the scala tympani (5) with only modest insertion forces. When in place, the dielectric members preferably touch the walls of the cavity into which they are inserted, thereby forming a series of separate longitudinal compartments (35), at least most of which contain at least one separate stimulating electrode. The dielectric members confine electrical currents injected through most of the contacts to flow preferentially through different portions of the wall of the cavity in which the electrode array is inserted, thereby selectively stimulating/activating cells encompassed by the compartments.

18 Claims, 7 Drawing Sheets

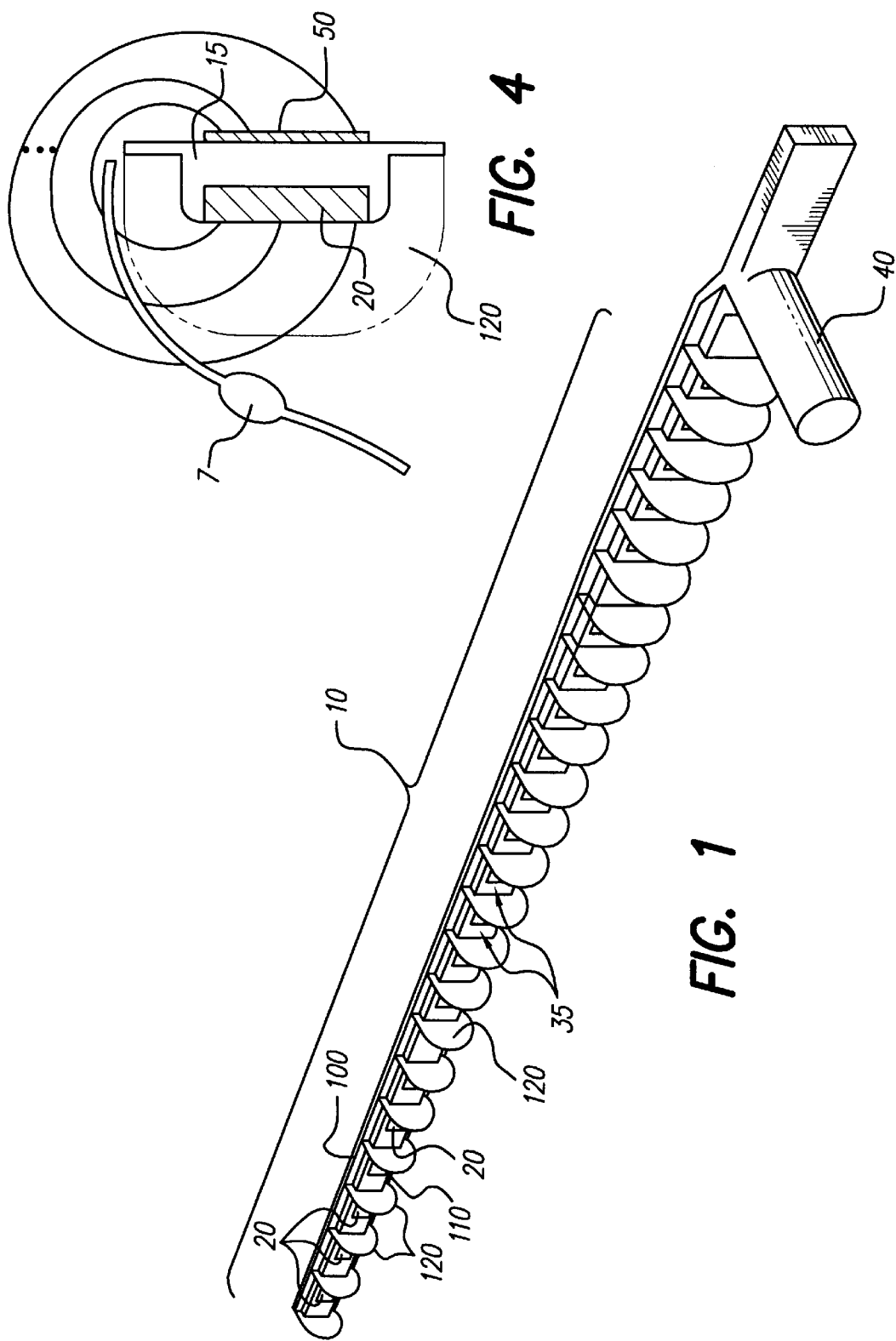

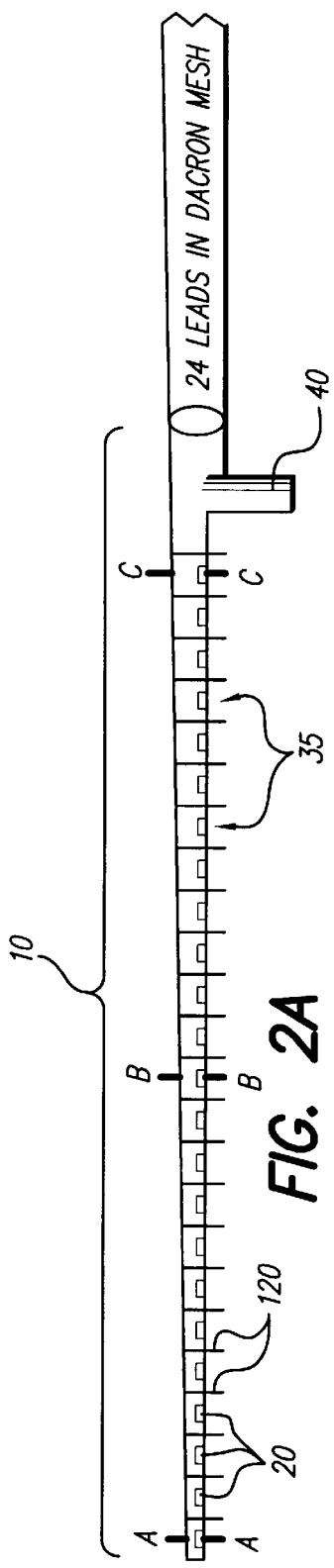
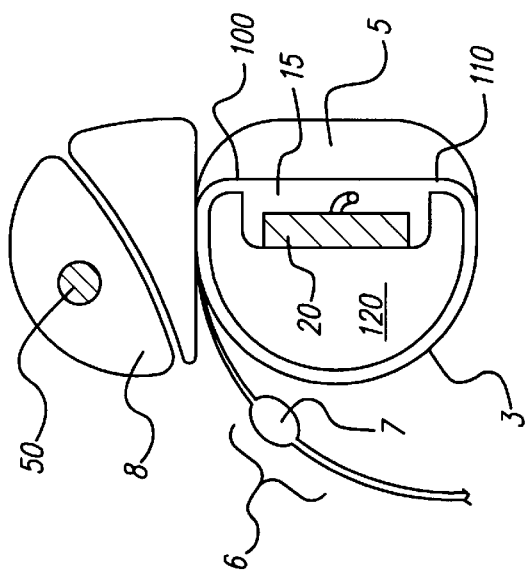
FIG. 2A
FIG. 2B
FIG. 2C
FIG. 3D

COCHLEAR ELECTRODE ARRAY EMPLOYING DIELECTRIC MEMBERS

This application is a continuation-in-part (CIP) of application Ser. No. 08/911,804, filed Aug. 15, 1997, now abandoned which is a CIP of PCT application Ser. No. PCT/US97/00936, filed in the PCT on Jan. 22, 1997, which PCT application designated the U.S. (among other countries); and which PCT application claims priority to U.S. provisional application Ser. No. 60/010,494, filed Jan. 24, 1996.

BACKGROUND OF THE INVENTION

The present invention relates to implantable stimulation devices, e.g., cochlear prothesis used to electrically stimulate the auditory nerve, and more particularly to an electrode array employing dielectric partitions or members that may be used with such implantable stimulating devices.

A cochlear prosthesis provides sensations of sound for patients suffering from sensorineural deafness. It operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis must perform the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

After extensive research in many centers employing a variety of surgical sites and approaches for the implantation of cochlear electrode arrays, a consensus has generally emerged on the use of the scala tympani, one of the three parallel ducts that, in parallel, make up the spiral-shaped cochlea. The electrode array to be implanted in this site typically consists of a thin, elongated, flexible carrier containing several longitudinally disposed and separately connected stimulating electrode contacts, perhaps 6–24 in number. Such electrode array is pushed into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site.

The selectivity of stimulation at each site provides a means for conveying different sound perceptions. Typically, cells (and their corresponding auditory nerve fibers) that are in one region or area convey sound perceptions within a given frequency band or channel. This selectivity of stimulation at each site provides a lower limit on the useful spacing available between adjacent sites. That is, if adjacent sites closer than that lower-limit spacing are stimulated simultaneously, then the signals carried by the neurons can no longer distinguish respective frequency bands separately, but rather will convey signals that are contaminated by cross-talk between channels and may be perceived as unclear and/or excessively loud. This lower-limit spacing also effectively limits the maximal number of parallel channels of information that can be conveyed about acoustic signals such as speech because the length of the scala tympani over which the complete range of speech signal frequencies is represented is fixed at about 15–20 mm in length. Further, the actual selectivity of stimulation at each site is limited by the spreading of the injected electrical current through the volume-conductive tissues and fluids of the cochlea.

Several stimulation strategies have been described in the prior art for maximizing the selectivity. These include:

Bipolar Stimulation—Bipolar stimulation provides two closely spaced electrode contacts within the scala tympani which are used to provide both a source and sink for the stimulating electrical current (see e.g., U.S. Pat. No. 4,819,647), instead of the monopolar configuration in which the sink for all channels is a common electrode located outside of the cochlea. With bipolar stimulation, the rate at which the current density decreases with distance from the electrodes is much greater than with monopolar stimulation. There is a significant disadvantage, however, in that the amount of current required to produce adequate stimulation at each site and the power required to pass that current through the tissues is much higher than for monopolar stimulation. This is a significant disadvantage for the efficient design and operation of implanted microminiature circuitry in a portable battery-powered system.

Directional Contacts—In some electrode designs, the individual contacts are shaped like cigar bands, causing the stimulating current to radiate in all directions equally. By using smaller contacts that occupy only a portion of the transverse crosssection of the electrode carrier at a particular longitudinal position, the current density can be made asymmetrical (see, e.g., U.S. Pat. Nos. 4,686,765; 4,819,647). If the design of the electrode array and its placement by the surgeon permits the contacts to be reliably positioned so as to be facing the medial wall of the scala tympani, in which the spiral ganglion cells reside, the selectivity will be somewhat improved. The improvement tends to be limited, however, by the tendency of stimulating current to disperse broadly through the relatively conductive fluids of the scala tympani. Furthermore, the small surface area of the contacts will increase their electrical impedance and, hence, the voltage required to deliver a particular stimulating current.

Spiral-Shaped Carriers—Regardless of the design of the electrode contacts and the tissues in which they reside, the current density is always highest nearest the contact surface. One strategy, therefore, that has been used with small contacts that face the medial wall is to embed them in an elastomeric carrier that is molded into the shape of the cochlear spiral (see U.S. Pat. Nos. 4,686,765; 4,819,647). Upon insertion, the carrier regains its spiral shape, drawing the contacts close to the medial wall. The fabrication of such an electrode array is somewhat complicated, however. Furthermore, special instruments and techniques must be used by the surgeon in order to hold the electrode straight in order to effect insertion into the round window opening.

Space-Filling Carriers—Yet another technique known in the art to position directional contacts near the medial wall is to make the electrode array relatively thick in cross-section. This can be done by using a mold whose dimensions are sized closely to the cross-sectional dimensions of the scala tympani (see U.S. Pat. Nos. 4,686,765; 4,819,647). Other techniques that achieve this same purpose could include adding flexible fins along the lateral edge to push the electrode towards the medial wall, or by making some or all of the carrier from a material that swells, inflates, or otherwise changes its dimensions after insertion. One problem with these techniques is that there is a fairly large range of variability in the dimensions of the scala tympani from one patient to another and there are often irregularities in cross-sectional area along the length of an individual scala tympani. As the electrode contacts get closer to the medial wall, even small fluctuations in the actual gap and the points of actual contact with the side walls can cause large changes in the distribution of the stimulating currents from each site, which may disrupt the orderly tonotopic representation and the balance of loudness between channels. Furthermore, the surgeon who performs the implant generally prefers an electrode that is as thin as possible to improve the chances of being able to insert it successfully in any conditions that may obtain.

Separate Contact Placements—Another technique for maximizing the selectivity of stimulation sites is to drill into the scala tympani through its lateral wall at multiple locations and place a separate stimulating electrode in each site, as described by Chouard and MacLeod (1976). Before sealing the holes, small plugs of a nonconductive material such as silicone elastomer are inserted into the holes so as to flank each electrode in an attempt to prevent its currents from spreading longitudinally in the conductive fluid of the scala tympani. Several problems developed with this technique that caused it to be abandoned. Only one side of the cochlear spiral is surgically accessible in this manner and even then, it is difficult to perform the multiple fenestrations without damaging the extremely delicate membranes that separate the three parallel canals. Further, even if accurately-sized plugs could be installed, they tend to block only longitudinal conduction and not lateral conduction out of the scala tympani and into adjacent, overlying turns of the spiral; in fact, the scar tissue that eventually seals over the fenestrations tends to be more conductive than the bone that it replaces, actually channeling stimulation currents laterally rather than in the desired medial direction.

Increases in the numbers of channels and the rates of stimulation in cochlear implants have exceeded the information carrying capacity of currently available electrode arrays. Cross-talk of stimulation between adjacent electrode sites limits the number of useful channels, particularly if more than one channel must be stimulated simultaneously to achieve reasonable repetition rates with power-efficient pulse widths. Furthermore, design features now available to improve channel selectivity (radial bipolar contact geometry, medial wall-hugging curvature and space-filling profile) also make the electrode more difficult to manufacture and to implant.

It is evident, therefore, that improvements are needed in cochlear electrodes to address the above and other concerns.

SUMMARY OF THE INVENTION

The cochlear electrode array that is the subject of the present invention includes a single elongated, tapered carrier on which a multiplicity of electrode contacts are carried. The electrode array is designed to be inserted into the scala tympani via an opening at or near the round window, in the conventional manner. A set of dielectric members, e.g., thin fins or bumps, project from the body of the carrier in particular axes. When these dielectric members are fins, they may be made of a highly flexible but resilient material that can be folded against the body of the carrier so as to slide past obstructions and to accommodate variations in the cross-sectional dimensions of the scala tympani. Alternatively, the dielectric members may be made from somewhat stiffer dielectric material formed as bumps or balls that glide over the surface of the cavity into which the electrode array is inserted. The fins or bumps or other dielectric members tend to form a "compartment" around each electrode array which focuses the stimulation current to remain within the area or volume encompassed by the compartment.

The electrode array of the present invention thus addresses the key to efficient and localized stimulation by delivering stimulation current from one electrode contact directly to the adjacent spiral ganglion cells before that current spreads longitudinally along the scala tympani. The electrode array achieves this key result by forming sets of transverse and longitudinal members that project from a thin, straight electrode body (made, e.g., from silicone). The fins or bumps generally mold themselves to the contours of the scala tympani. Each of the electrode contacts, which are preferably made from Pt—Ir, is located in a separate compartment thus created within the cochlea. The leads from the contacts are gathered into a flattened rib within the thin, molded silicone body, thereby permitting the electrode to flex readily but only in the axis of the cochlea spiral. The electrode contact itself is molded in a straight configuration that is readily inserted through a small cochleostomy and positioned so that all contacts face the spiral ganglion.

An important advantage achieved with the cochlear electrode array of the present invention is that the insertion forces required in order to insert the electrode array into its desired position within the cochlea are less than is required to insert other cochlear electrode arrays of the prior art. Being able to insert the electrode array with less force advantageously reduces the risk of injury or damage to the cochlea.

In one preferred embodiment, the dielectric members comprise flexible fins which are extensions of the silicone elastomer that forms the body of the carrier and are molded as one with the body of the carrier in a single injection molding process. In other embodiments, the dielectric members comprise somewhat thicker and stiffer bumps or partitions that may be formed integrally with the carrier, or added to the carrier, employing a variety of other materials and processes as is known in the art.

In accordance with one aspect of the invention, the fins or bumps or other partitions should be made of a dielectric material, i.e. a material with a much higher resistivity to electrical current than any of the surrounding tissues of the cochlea. When fins are used, they are designed so that upon insertion, the elastic fins unfurl so that they touch the walls of the scala tympani, effectively separating it into a series of separate longitudinal compartments, each of which contains a separate stimulating electrode. When bumps are used, they too are designed to touch the walls of the scala tympani to form separate compartments. Because the fins or bumps or other partitions have a much higher resistivity than the surrounding tissue, current can flow to or from the electrode in each compartment only through the portion of the wall of the scala tympani that lies within that compartment, thereby enhancing the selectivity of the spiral ganglion cells adjacent to that compartment.

It is a feature of the invention to provide a cochlear electrode array that produces a predictable and highly selective activation of spiral ganglion cells at each of a large number of closely spaced sites along the longitudinal axis of the cochlea.

It is a further feature of the invention to provide a cochlear electrode array that is readily insertable in scala tympani that have a wide range of dimensions and even partial obstructions.

It is yet an additional feature of the invention to provide a cochlear electrode array that can be inserted into the cochlea with a minimal insertion force.

It is another feature of the invention to provide a cochlear electrode array that has a minimal likelihood of producing damage to the cochlea upon its initial insertion, after prolonged function, and even in the event that surgical removal and/or replacement is required.

It is yet an additional feature of the invention to provide a cochlear electrode array that minimizes the electrical power required to achieve adequate stimulation and perceived loudness.

It is still another feature of the invention to provide a cochlear electrode array that is readily manufacturable.

It is an object of the finned design of the present invention to facilitate the a traumatic insertion of the electrode to the designed depth. It is a further object to facilitate insertion of the electrode to whatever depth is necessary to obtain the desired electrical partitioning produced by the transverse fins engaging the sidewalls. It is another object to permit the electrode to be inserted past local obstructions within the scala tympani, such as partial obstructions by bone or scar tissue, local irregularities in the walls, or restrictions in the dimensions of the round window cochleostomy itself through which the electrode is introduced.

BRIEF DESCRIPTION OF THE DRAWINGS

The above and other aspects, features, objects and advantages of the present invention will be more apparent from the following more particular description thereof, presented in conjunction with the following drawings, wherein:

FIG. 1 shows a perspective view of an electrode array made in accordance with one embodiment of the present invention;

FIG. 2A is a top schematic representation of the electrode array of FIG. 1;

FIG. 2B is an expanded sectional view of one of the compartments of the electrode array;

FIG. 2C is an expanded front view of one of the compartments of the electrode array;

FIG. 3D shows the desired fit of the apical cross-section A—A in the scala tympani;

FIG. 4 shows a cross-sectional view of an alternative embodiment of the invention that includes an additional elongated electrode contact that may be used as a reference or return electrode;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

It should be noted that while the description that follows is directed to a cochlear electrode array, which represents the preferred embodiment of the invention, the electrode array may be used for applications other than stimulating the cochlea. In general, the invention may be used with any type of electrode array that needs to be inserted into a body cavity using a minimal insertion force.

An example of a prior electrode array, and the manner of making such an array, is taught in U.S. Pat. Nos. 4,686,765 and 4,819,647, both of which are incorporated herein by reference. Many of the teachings of these patents, e.g., regarding physiology of the cochlea, materials for the electrodes and carrier/body, manufacturing techniques, sizes, dimensions of the scala tympani, etc., apply equally well to the present invention.

A preferred embodiment of an electrode array 10 made in accordance with the invention is shown in FIGS. 1, 2A, 2B, and 2C. FIG. 1 shows a perspective view of the electrode array 10; FIG. 2A is a top schematic representation of the electrode array 10; FIG. 2B is an expanded top view of one small section or compartment 3 5 of the electrode array 10; and FIG. 2C is an expanded front view of one of the compartments 35 of the electrode array.

Figure 3A:
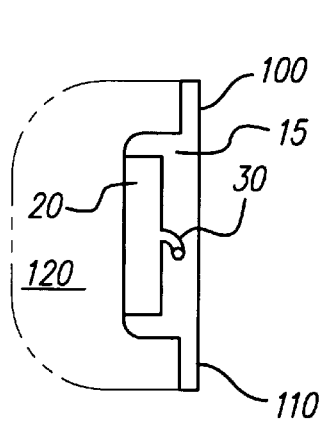
FIG. 3A is a cross-sectional view taken along the line A—A in FIG. 2A.
Figure 3B:
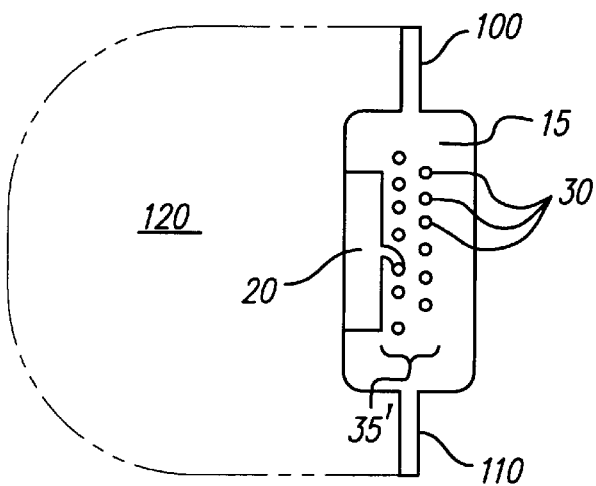
FIG. 3B is a cross-sectional view taken along the line B—B in FIG. 2A.
Figure 3C:
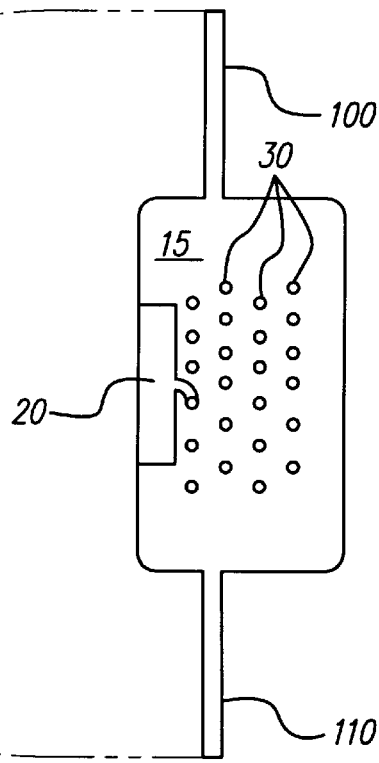
FIG. 3C is a cross-sectional view taken along the line C—C in FIG. 2A.

As seen in FIGS. 1, 2A, 2B and 2C, the electrode array 10 includes a body 15, a multiplicity of individual contacts 20 for example, at least six contacts, and their associated wire leads 30 coursing through the body 15, plus fins 100, 110, and 120. The outside dimensions of the electrode array plus fins at various points along the length of the array is carefully sized so as to be at least slightly larger than available cross-sectional dimensions of the scala tympani in most human beings. Typical cross-sectional profiles at three points along the array, designated A—A, B—B and C—C in FIG. 2A, are shown in FIGS. 3A, 3B and 3C, respectively.

After insertion of such an electrode 10 to the intended depth in the scala tympani, the various fins will touch and be somewhat bent or compressed by their contact with the walls of the scala tympani. The desired fit of the apical cross-section A—A in the scala tympani is shown in FIG. 3D.

In the preferred embodiment that is illustrated in the figures, the fins lie in only two axes. One pair of fins 100 and 110 projects perpendicularly from the body so as to create a longitudinal barrier in the vertical axis of the spiral. It is a feature of this arrangement that any stiffness contributed by fins 100 and 110 contributes to the desired property of the electrode array that it flex readily in only this vertical axis, particularly in the more apical regions of the scala tympani where the electrode array must curl tightly along this axis to conform to the spiral shape of the cochlea. This flexion property is further enhanced in the preferred embodiment by the gathering of leads 30 into a vertically aligned "rib" 35' as illustrated in the cross-sectional view in FIG. 3B.

A multiplicity of fins 120 project perpendicularly from body 15 in the medial direction of the transverse plane, lying orthogonal to and joining with fins 100 and 110. Transverse fins 120 effectively divide the scala tympani 5 (seen in FIG. 3D) into a set of longitudinally separate compartments 35 (FIGS. 2A, 2B) within each of which there is one individual electrode contact 20. When all of the various fins have unfurled so as to touch the walls of the scala tympani as shown in FIG. 3D, the electrical current injected from each contact must pass through the bone that forms the medial wall 3 (FIG. 3D) of each separate compartment, and thence into the subjacent portion of the spiral ganglion 6. Thus, all or most of the stimulating current delivered to a given contact tends to be directed to, and hence flow through, the spiral ganglion, where it can effectively stimulate the auditory neurons 7, rather than being dissipated in other paths that do not intersect these neurons.

Also shown in FIG. 3D is an elongated electrode contact 50 that is inserted into the scala vestibuli 8 so as to provide a return pathway for stimulation current injected into the cochlea from one or more individual contacts 20. Elongated electrode contact 50 lies parallel to all or much of the length of electrode array 10. This arrangement further enhances the tendency of stimulation currents to flow parallel to spiral ganglion neuron 7 stimulating them efficiently and selectively.

It should be appreciated that transverse fins 120 add little or no stiffness to the electrode array 10 in the axis along which the array must flex to accommodate the cochlear spiral. Furthermore, the transverse fins can be bent or furled in either longitudinal direction so that the electrode array can slide out of the scala tympani even if connective tissue grows into some or all of the various compartments 35 created between the fins. A tab 40 (FIG. 2A) projecting from the array at its basal end can be used as a handle whereby the surgeon pushes or pulls the electrode array to effect insertion or removal of the electrode array. The tab 40 also provides a marker indicating that the electrode array has been inserted to the intended depth when the tab 40 is aligned with the round window opening.

In another embodiment of the invention shown in FIG. 4, an elongated electrode contact 50 is added to the lateral surface of body 15 along all or most of the length of the array (e.g., along the back side of the array in the region between sectional lines A and C of FIG. 2A). This elongated electrode contact 50 may be used as the return electrode for some or all of the stimulating pulses applied to individual contacts 20. As described in a separate patent, U.S. Pat. No. 5,649,970, Ser. No. 08/516,758, filed Aug. 18, 1995, which patent is incorporated herein by reference, this arrangement causes each site of stimulation to behave in a quasi-bipolar mode, further reducing any tendency for stimulation current to spread longitudinally. This arrangement also increases the tendency for the current (designated "i" in FIG. 4) flowing through the spiral ganglion to follow a course that lies parallel to the elongated processes of neurons 7, which is more efficient for activating those neurons.

The electrode contacts 20 and 50, if present, may be made of any biocompatible electrode material such as platinum and its alloys, iridium or anodized tantalum. The associated electrode leads 30 may be made of any similarly biocompatible conductive material. The mechanical properties, shape and dimensions of leads 30 and their disposition within body 15 can be used to modify the flexibility and other handling properties of the electrode array 10 so as to improve its insertability into the scala tympani. For example, it may be advantageous to use one or more different calibers of individual round or flattened wires with various of the apical or basal contacts, or to use a ribbon cable in which a multiplicity of wires are held together by bonds or envelopments of dielectric material.

Alternatively or additionally, some or all of body 15 may be fabricated from a stiffer material than the material used for fins 100, 110 and 120. This can be accomplished. for example, by molding body 15 as a preform from a silicone elastomer having a relatively high durometer value and then inserting this preform into the mold used to add fins made from a lower durometer elastomer. (Note: the "durometer is a measure of the hardness of elastomeric materials such as silicone. Durometer value 40 is a soft, flexible rubbery material suitable for the fins. Durometer value 80 is a hard, stiff rubber such as might be suitable in the body of the electrode or the preform.) It may be advantageous for the preform to contain various wells, pockets or other shape features to facilitate the placement of contacts 20 and leads 30 during fabrication of electrode array 10.

It is desirable for the electrode array 10 to be relatively stiff in all directions at the basal end of the electrode array 10, a cross-sectional view of which basal end is shown in FIG. 3C. In order to achieve this, the relatively large number of electrode leads 30 present at this point are dispersed throughout the relatively thick body 15 rather than gathering into a rib 35 as illustrated in FIG. 3B.

Both human and cat versions of the "compartmental" electrode of the present invention have been fabricated using micro-machined injection molds. In vivo tests of the cat electrode and in vitro tests of the human electrode have confirmed the desired surgical handling properties (e.g., low insertion forces) and have further demonstrated the predicted effects of the fins on electrode impedance. In particular, seating of the fins against the walls of the scala tympani have produced large increases in monopolar and adjacent bipolar impedances, consistent with a reduction of longitudinal shunt currents.

Figure 5:
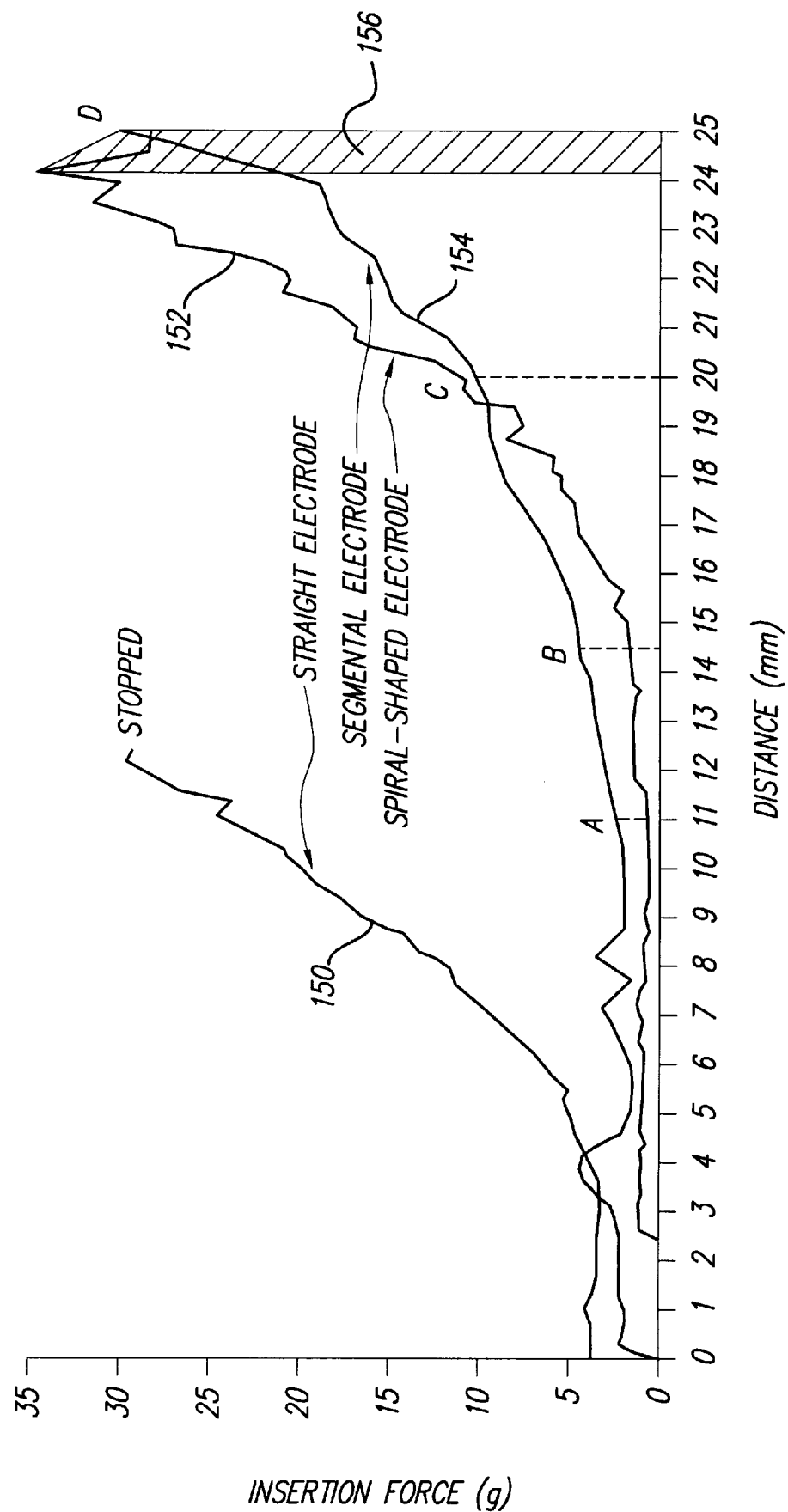
FIG. 5 is a graph that compares the insertion force required to insert the electrode array of the present invention compared to other electrode arrays of the prior art.

FIG. 5 is a graph that compares the insertion forces needed to insert the compartmental electrode of the present invention with the insertion forces required to insert a straight electrode of the prior art (curve 150), a spiral electrode of the prior art (curve 152), and the electrode of the present invention (curve 154). The data presented in FIG. 5 show that the insertion (pushing) force required to fully insert the finned electrode (Note, that the electrode of the present invention may be variously called the "finned" electrode, the "compartmental" electrode, or the "segmental" electrode) is lower than has been measured for any other cochlear electrode to date. The curves compare the force profile of the finned electrode (curve 154) to the prior art preformed spiral electrode (curve 152) and to a straight electrode (curve 150). The spiral electrode (curve 152) tends to have very low insertion forces until its preformed curvature becomes greater than the accelerating curvature into which it is being pushed, whereupon the electrode bows against the outside walls (which is undesirable electrically) and the insertion force rises rapidly. Straight electrodes (curve 150) tend to hit the back wall of the first turn at around 10 mm and then require large forces to deform them into the cochlear curve. In the case shown in FIG. 5, insertion was stopped when the force reached 30 g. Normally, clinicians would push harder to complete insertion to 20–24 mm, with the risk of damage to the basilar membrane or osseous spiral ligament attaching the basilar membrane to the lateral wall of the scala tympani. Such damage, if accompanied by endolymph leakage, tends to cause local destruction of the spiral ganglion cells which the cochlear electrode seeks to stimulate.

FIG. 5 thus shows that the insertion force required to insert an electrode array into a human cochlea to a depth of at least 20 mm is less than 15 g; and to a depth of at least 24 mm is less than 20 to 25 g.

Still with reference to FIG. 5, the finned electrode (curve 154) requires a low but steady force throughout its insertion, rising with a gradual slope as it reaches full designed insertion depth. (The hatched region 156 denotes the end of the acrylic mold, where the electrode is being pushed against a stop that does not exist in the normal cochlea). The finned electrode is designed to ride on the longitudinal fins, which tend to hold the stiffer body containing the leads and contacts away from the lateral wall. These fins slide easily along the walls because they are extremely soft and deformable, allowing them to undulate and walk into new positions even if held locally and temporarily by friction. Such fins also slide gracefully past local obstructions within the scala tympani. These include ectopic bone or other scar tissue left by previous infections, irregularities in the wall profile left during development (such as is known to occur in some cochleas where the scala tympani crosses the facial nerve), and the relatively small access hole afforded by opening only the round window itself (using a small cochleostomy procedure known as "soft surgery" and favored by some surgeons as faster and less potentially dangerous to the cochlea).

It should be noted that the finned electrode could likely be inserted to greater depths than the mold permits. This could be useful for permitting the transverse fins to engage properly the medial wall of the scala tympani despite variations in dimensions of the scala tympani. Because the scala tympani is a gradually tapering cavity, the finned electrode can be pushed in until the fins engage the sidewalls. This could be determined either by an apparent increase in insertion force or by monitoring of the electrode impedances, which rise abruptly when the fins engage the walls and therefore minimize longitudinal current spread from each contact, as seen in FIGS. 6A, 6B, 7A, and 7B, presented below.

It is thus seen that the present compartmental electrode may be inserted to a greater depth within the cochlea with less insertion force than can prior art electrodes.

Figure 6A:
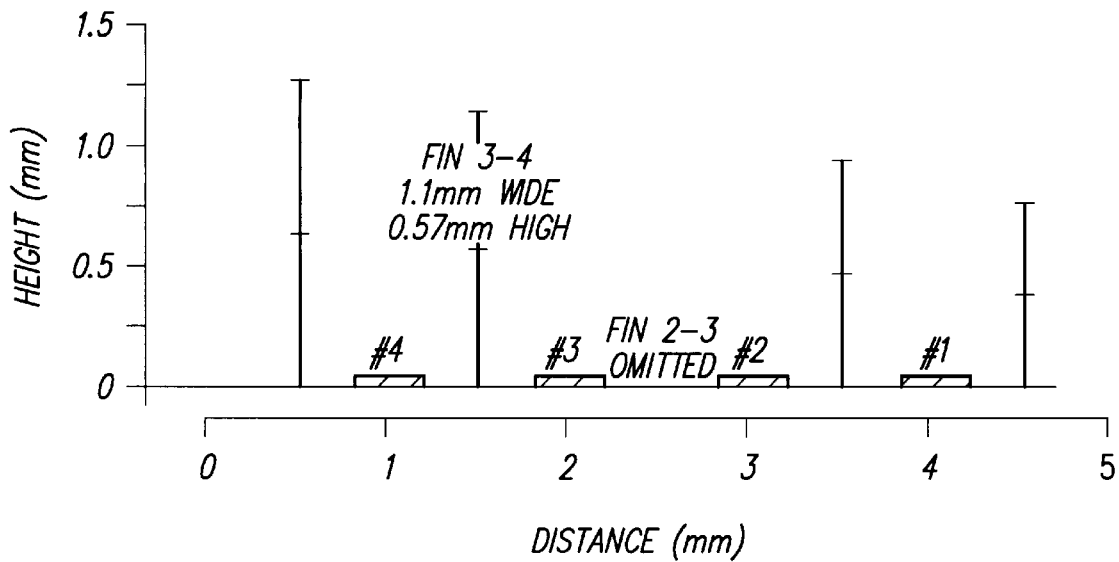
FIG. 6A shows the height, width and spacing of four fins separating four electrodes which were used to measure electrode impedance.
Figure 6B:
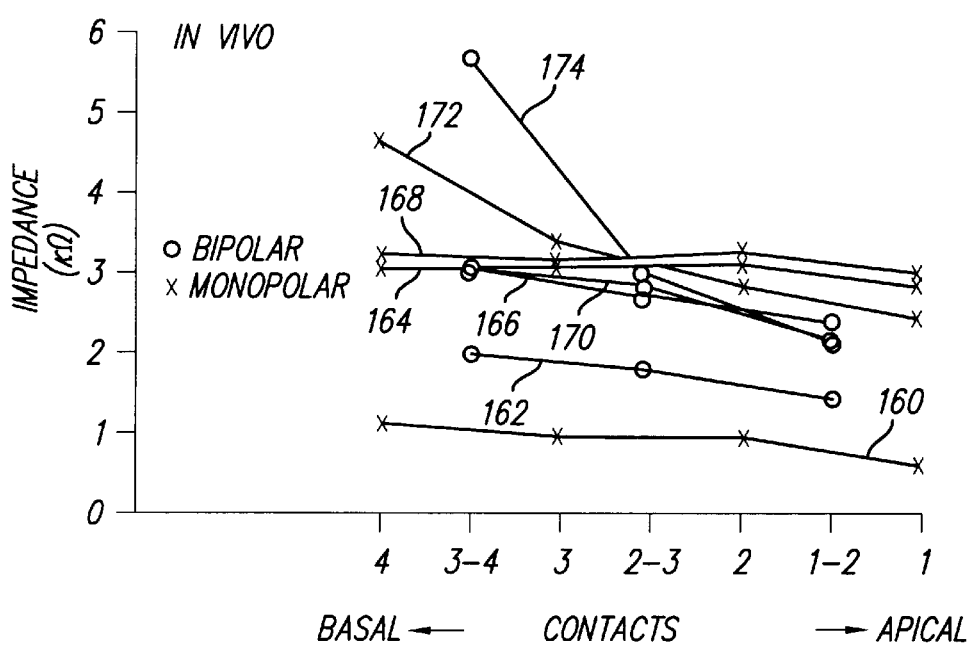
FIG. 6B shows the impedance data obtained using the four electrodes and associated fins of FIG. 6A.

Turning next to FIGS. 6A and 6B, electrode impedance data for a cat version of the compartmental electrode of the present invention is shown at various depths and configurations (bipolar or monopolar). FIG. 6A shows the height, width and spacing of four fins separating four electrodes which were used to measure electrode impedance. The electrodes are numbered #1, #2, #3 and #4, with electrode #1 being the electrode that is inserted the farthest, 4 mm. The fins are referenced by the electrode numbers on either side. Thus, fin 3–4 is the fin that separates electrode #3 and electrode #4; and fin 1–2 is the fin that separates electrode #1 and electrode #2. For purposes of the in vivo impedance tests conducted using the cat version of the electrode, fin 2–3 was omitted.

The impedance data obtained using the cat version of the compartmental electrode of the present invention is shown in FIG. 6B. Both monopolar and bipolar impedance measurements were made. A bipolar impedance was measured between adjacent electrodes, e.g., between electrode #4 and electrode #3, whereas monopolar impedance was measured from a single electrode, e.g., electrode #3, to a common ground electrode. For purposes of the impedance data presented in FIG. 6B, a monopolar impedance data point is thus presented above a single electrode contact on the horizontal axis, e.g., "4"; whereas a bipolar impedance data point is presented intermediate two electrode contacts, e.g., "3–4".

As seen in FIG. 6B, a monopolar baseline impedance in a saline solution (curve 160) remains relatively constant at about 1 K$\Omega$; and a bipolar baseline impedance in a saline solution (curve 162) also remains relatively constant at about 2 K$\Omega$. At depth 1, both the monopolar (curve 164) and bipolar (curve 166) impedances are approximately 3 K$\Omega$ or a little less. At depth 2, the monopolar (curve 168) and bipolar (curve 170) impedances remain approximately at this same value, e.g., about 3 K$\Omega$. At depth 4, however, which is the full insertion depth, it is seen that the monopolar impedance (curve 172) jumps to about 4.5 K$\Omega$ (for electrode #4), and the bipolar impedance between electrodes #3–#4 raises to about 5.5 K$\Omega$. Thus, it is seen that the electrode impedance rises significantly when the fins reach the proper depth.

Figure 7A:
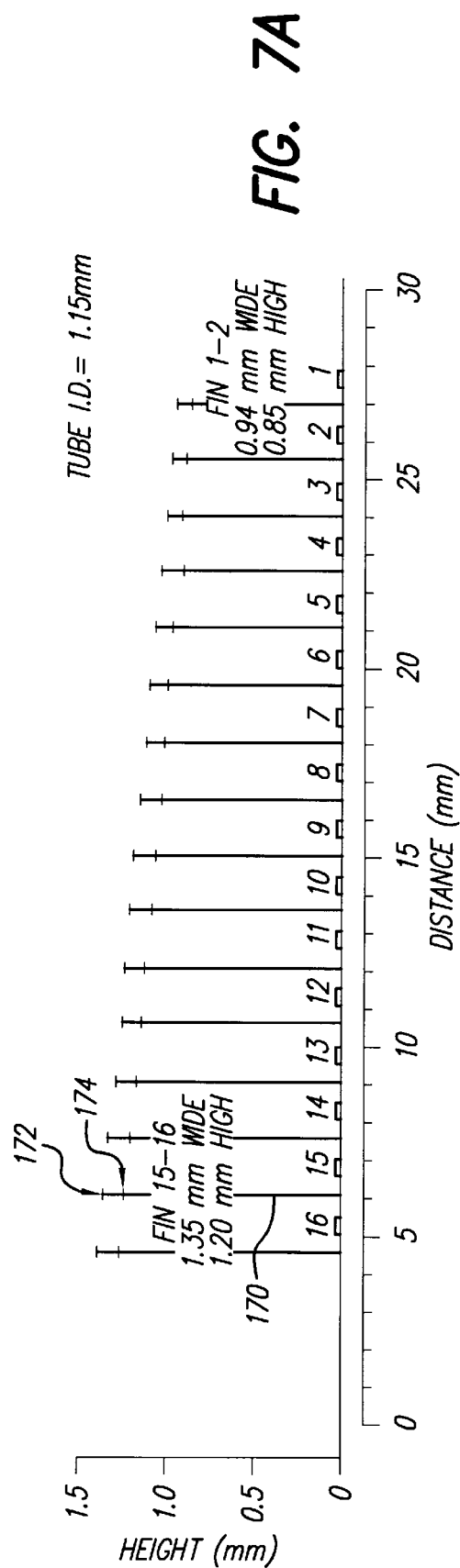
FIG. 7A shows the height, width and electrode spacing of sixteen fins and sixteen electrodes used to measure electrode impedance.
Figure 7B:
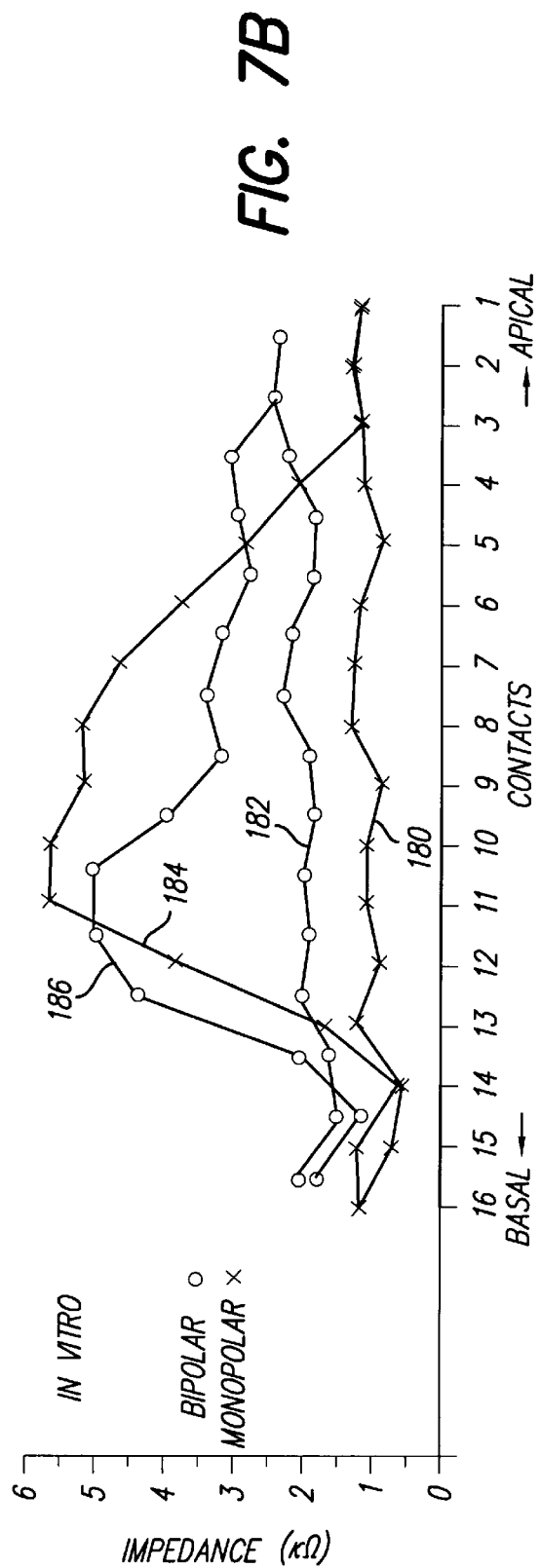
FIG. 7B shows the impedance data obtained using the sixteen electrodes and associated fins of FIG. 7A.

Turning next to FIGS. 7A and 7B, similar data is presented for a finned electrode that has sixteen fins and sixteen electrodes. The electrodes and fins are identified in FIGS. 7A and 7B in the same way as is used in FIGS. 6A and 6B. FIG. 7A shows the height, width and electrode spacing of such electrode, and FIG. 7B shows the in vitro impedance data obtained using the sixteen electrodes and associated fins of FIG. 7A. For the in vitro data shown in FIG. 7B, a tube, having an inside diameter of 1.15 mm, was used to simulate the human cochlear.

As seen in FIG. 7A, the height and width of the sixteen fins tapers gradually from the 1.35 mm wide, 1.20 mm high, "15–16" fin to the 0.94 mm wide, 0.85 mm high, "1–2" fin; with the top 172 of the fin line, e.g., fin line 170 (representing fin 15–16) representing the width of the fin and the marker 174 representing the height of the fin. As the data in FIG. 7B show, the baseline monopolar impedance data in saline solution (curve 180), as well as the baseline bipolar impedance data in saline solution (curve 182) remain relatively flat at values of approximately 1 K$\Omega$ and 2 K$\Omega$, respectively, regardless of insertion depth. However, the monopolar impedance (curve 184) and the bipolar impedance (curve 186) rise dramatically, e.g., up to 5 K$\Omega$ or 6 K$\Omega$, respectively, once insertion has taken place.

It is thus seen that the electrode impedance rises significantly once insertion in the cochlea has occurred to a desired depth. Measuring the electrode impedance thus provides one way of determining when a desired insertion depth has been reached.

Figure 8A:
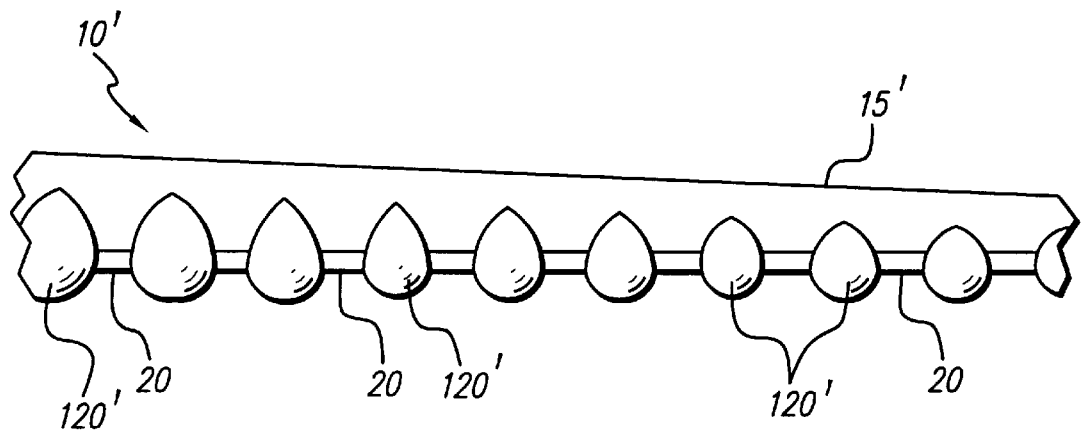
FIGS. 8A and 8B illustrate plan and side views, respectively, of an alternative embodiment of an electrode array made in accordance with the invention, wherein dielectric members or bumps are used to separate its respective electrodes.
Figure 8B:
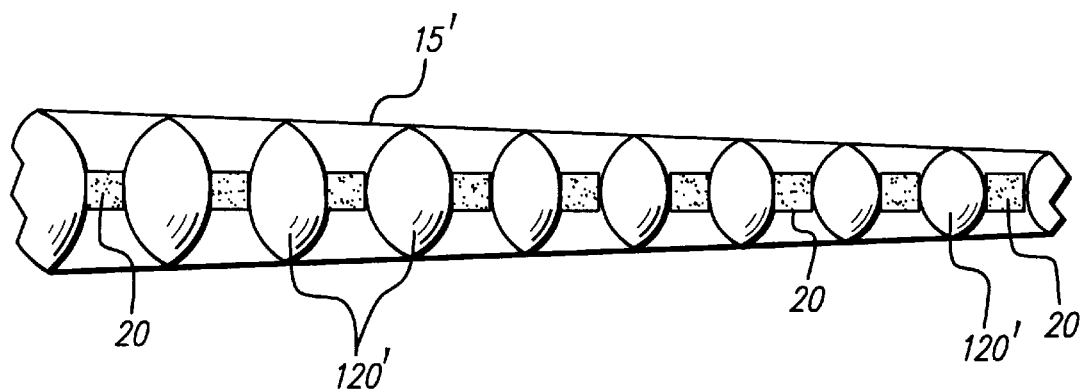

Turning next to FIGS. 8A and 8B, there is shown a plan (e.g., top) and side view, respectively, of a portion of an alternative embodiment of an electrode array 10' made in accordance with the invention. In most material respects, the array 10' is basically the same as the array 10 previously described except that the fins 120 utilized with the prior embodiment are replaced by dielectric bumps 120'. Such bumps 120' are preferably formed as an integral part of the array body 15' so as to be intermediate the individual electrode contacts 20. Further, the top fin 100 and bottom fin 110, utilized in the prior embodiment, see FIGS. 1, 2A, 2B and 2C, may or may not be employed, as circumstances dictate. Such top and bottom longitudinal fins are not shown in FIGS. 8A and 8B, but it is to be understood that such fins 100 and 120 could be employed, if desired.

Like the fins 120 previously described, the dielectric bumps 120' create individual partitions surrounding each electrode contact 20, thereby helping to confine the electrical stimulus charge to such individual compartments, whereby the charge is more likely to pass through the bone that forms the medial wall of each individual compartment. When the electrode array 10' is a cochlear electrode array, intended for insertion into the scala tympani of the cochlea, the cross section of the electrode array 10', with its bumps 120', is preferably about the same size as the cross-section of the scala tympani, or less. If significantly less, a positioner may be used behind the electrode array in order to force the bumps against the medial wall of the scala tympani, as described in U.S. patent application Ser. No. 60/087,653, filed Jun. 2, 1998, assigned to the same assignee as is the present application. The referenced patent application, Ser. No. 60/087,653, is incorporated herein by reference.

As evident from the preceding description, the present invention thus provides a finned or other dielectric-member (e.g., bumps) design for a cochlear electrode that facilitates the a traumatic insertion of the electrode to the designed depth. It is further seen that the insertion of such electrode to whatever depth is necessary to obtain the desired electrical partitioning produced by the transverse fins engaging the sidewalls is facilitated. Moreover, it is seen that because of the flexibility of the fins, the electrode may be readily inserted past local obstructions within the scala tympani, such as partial obstructions by bone or scar tissue, local irregularities in the walls, or restrictions in the dimensions of the round window cochleostomy itself.

While the invention herein disclosed has been described by means of specific embodiments and applications thereof, numerous modifications and variations could be made thereto by those skilled in the art without departing from the scope of the invention set forth in the claims.

What is claimed is:

1. An electrode array (10) adapted for insertion into a scala tympani of a cochlea for nerve stimulation comprising:
    a flexible body (15);
    a multiplicity of spaced-apart, electrode contacts (20) carried by said body, each electrode contact having a wire connected thereto through which electrical contact with each electrode contact is established, the wires being embedded within the flexible body; and
    a plurality of fins (100, 110, 120) attached to the flexible body, the fins comprising permanent, compliant, dielectric material that projects from said body, the outside dimension of said array plus said fins being equal to or greater than the typical cross-section of the scala tympani in which said electrode array is adapted to be inserted;
    wherein the number of electrode contacts carried by said flexible body comprises at least six, and wherein at least one fin resides between each adjacent electrode contact.

2. The electrode array of claim 1 wherein said fins comprise orthogonal fins lying in two axes; a first set of fins projecting substantially perpendicularly from the longitudinal axis of the flexible body so as to create a longitudinal barrier in a vertical axis; and a second set of fins, generally orthogonal to and joining the first set of fins, that project substantially perpendicularly from the body in a medial direction of a transverse plane; said fins effectively defining a set of longitudinally separate compartments, wherein one electrode contact resides in each separate compartment.

3. The electrode array of claim 1 wherein the flexible body is made from a first material and the fins are made from a second material, and wherein the first material has a stiffness greater than the stiffness of the second material.

4. The electrode array of claim 1 wherein the wires embedded within the flexible body are gathered to form a rib in at least those regions of the electrode array between a tip and midpoint of the electrode array.

5. The electrode array of claim 1 wherein the wires embedded within the flexible body are dispersed throughout a proximal end of the flexible body.

6. The electrode array of claim 1 further including an elongated electrode contact (50) insertable into the scala vestibuli so as to provide a return pathway for stimulation current applied to one or more of said electrode contacts (20) through said wires.

7. An electrode array (10) insertable into a cochlea comprising:
    a multiplicity of spaced-apart electrode contacts (20), each having at least one wire connected thereto through which an electrical connection is established with the electrode contact and
    a multiplicity of dielectric fins (100, 110, 120) wherein each electrode contact is surrounded on at least three sides by said multiplicity of dielectric fins.

8. An electrode array insertable into a human cochlea comprising:
    a multiplicity of spaced-apart electrode contacts, each having at least one wire connected thereto through which an electrical connection with the electrode contact is selectively made and
    a Plurality of fins comprising a compliant, dielectric material formed around each electrode contact, wherein the fins can bend and fold, whereby during insertion of said electrode array into the cochlea, the fins bend and fold to provide a minimal insertion force.

9. The electrode array of claim 8 wherein the minimal insertion force provided by the bendable and foldable fins for an insertion depth of at least 20 mm is less than about 15 g.

10. the electrode array of claim 8 wherein the minimal insertion force provided by the bendable and foldable fins for an insertion depth of at least 24 mm is less than about 25 g.

11. The electrode array of claim 10 wherein the minimal insertion force provided by the bendable and foldable fins for an insertion depth of at least 24 mm is less than about 20 g.

12. An electrode array insertable into a body cavity for nerve stimulation comprising:
    a flexible body;
    a multiplicity of spaced-apart, electrode contacts carried by said body, each electrode contact having at least one wire electrically connected thereto, each of the wires being embedded within the flexible body; and
    permanent dielectric members projecting from said body in the space between adjacent ones of the spaced-apart electrode contacts, wherein the outside dimension of said array plus said members is approximately equal to the typical cross-section of the cavity in which said array is insertable.

13. The electrode array of claim 12 wherein the body cavity in which the electrode array is insertable comprises a scala tympani of a cochlea, wherein the electrode array comprises a cochlear electrode array, and wherein the electrode contacts of the array are spaced apart so that when energized they may selectively stimulate neurons of the auditory nerve.

14. The electrode array of claims 12 wherein the number of electrode contacts comprises at least six, and wherein at least one dielectric member resides on each side of each electrode contact except for an end electrode contact.

15. The electrode array of claim 12 wherein the dielectric members comprise dielectric members projecting from the longitudinal axis of the flexible body in a medial direction, said dielectric members effectively dividing the cavity into which the electrode array is insertable into a set of longitudinally separate compartments or regions, within at least most of which resides one of said electrode contacts.

16. The electrode array of claim 12 wherein the flexible body is made from a material that is stiffer than the material from which the dielectric members are made.

17. The electrode array of claim 12 wherein the wires within the flexible body are gathered to form a rib in at least those regions of the electrode array between a tip and a midpoint of the electrode array.

18. The electrode array of claim 12 further including an elongated electrode contact (50) insertable into the scala vestibuli so as to provide a return pathway for stimulation current injected into the cochlear from one or more of said electrode contacts (20).

* * * * *